United States Patent
Barnes et al.

(10) Patent No.: US 11,932,450 B1
(45) Date of Patent: Mar. 19, 2024

(54) SMALL SCREW CATCHMENT AND CADDY SYSTEM

(71) Applicants: Bryan Barnes, Athens, GA (US); Jaime Dodge, Athens, GA (US)

(72) Inventors: Bryan Barnes, Athens, GA (US); Jaime Dodge, Athens, GA (US)

(*) Notice: Subject to any disclaimer, the term of this patent is extended or adjusted under 35 U.S.C. 154(b) by 0 days.

(21) Appl. No.: 18/377,008

(22) Filed: Oct. 5, 2023

(51) Int. Cl.
*B65D 25/10* (2006.01)
*A61B 17/86* (2006.01)
*A61B 50/20* (2016.01)
*F16B 41/00* (2006.01)

(52) U.S. Cl.
CPC .......... *B65D 25/108* (2013.01); *A61B 17/865* (2013.01); *A61B 50/20* (2016.02); *F16B 41/002* (2013.01)

(58) Field of Classification Search
CPC ....... A61B 17/865; A61B 50/20; A61B 17/86; A61B 17/8038; A61B 17/8042; A61B 17/8047; F16B 41/002; B65D 25/108; B65D 25/10
USPC ........ 206/349, 206, 207, 210, 6.1, 363, 368, 206/379, 372, 338, 339, 438; 606/300–302
See application file for complete search history.

(56) References Cited

U.S. PATENT DOCUMENTS

| | | | |
|---|---|---|---|
| 7,350,643 B2 * | 4/2008 | Capanni | A61B 90/50 206/370 |
| 7,650,991 B2 | 1/2010 | Hester et al. | |
| 8,061,517 B2 * | 11/2011 | Loeffler | A61B 90/94 206/347 |
| 8,240,731 B2 | 8/2012 | Roszak | |
| 9,005,206 B2 * | 4/2015 | Ampuero | A61B 17/8695 606/86 R |
| 2012/0138495 A1 * | 6/2012 | Bettenhausen | A61B 50/30 206/339 |
| 2014/0309702 A1 * | 10/2014 | Wand | A61B 50/20 206/339 |
| 2021/0267650 A1 * | 9/2021 | Didyk | A61B 50/20 |
| 2023/0052702 A1 * | 2/2023 | Momany | A61B 50/30 |

FOREIGN PATENT DOCUMENTS

WO    WO-2015066467 A2 *  5/2015  ........... A61B 17/865

* cited by examiner

*Primary Examiner* — Rafael A Ortiz
(74) *Attorney, Agent, or Firm* — Meunier Carlin & Curfman LLC

(57) ABSTRACT

A screw containment system is disclosed including a caddy, a first screw, an adhesive substance, and a cover. The caddy includes a plurality of recesses including a first recess extending from a first opening towards a second surface of the caddy. The first recess is sized to accept a screw therein and includes a counterbore at a distal end. The first screw is removably disposed in the first recess such that the screw head shoulder sits on an upper surface of the counterbore with the shank disposed in an inner recess of the counterbore. The adhesive substance is disposed within the drive of the first screw, the adhesive substance being configured to temporarily couple two objects together. The cover is removably coupled to the first surface of the caddy such that, while the cover is coupled to the first surface, the first screw held within the first recess.

9 Claims, 5 Drawing Sheets

SMALL SCREW CATCHMENT AND CADDY SYSTEM

BACKGROUND

Picking up small screws while repairing or manufacturing delicate devices, such as eyeglasses, watches, or jewelry components, can be a frustrating and challenging task. Small-diameter screw systems used in spinal surgery, cranial plating, and oral and maxillofacial surgery present similar challenges. These screws are often minuscule, sometimes measuring just a few millimeters in length, making them nearly invisible to the naked eye. Their diminutive size and lightweight nature make them susceptible to getting lost or easily dropped, adding to the complexity of the task. Furthermore, the screws are often made of materials like stainless steel or brass, which can be highly reflective, causing them to blend into the background or become camouflaged against the surface they fall on. This optical illusion makes locating them an exercise in patience and keen observation.

Additionally, the small screws are prone to rolling or bouncing away when dropped, further complicating the retrieval process. Their tiny size also makes it difficult to grasp them using traditional tools or fingers, requiring the use of specialized tweezers or magnifying glasses to enhance visibility and precision. Repairing or manufacturing small devices, like eyeglasses, watches, or jewelry components, demands a steady hand, meticulous attention to detail, and an abundance of patience. The same level of expertise that is required for small-diameter screw systems is also required in spinal surgery, cranial plating, and oral and maxillofacial surgery systems. The search for and placement of these minuscule screws can be a time-consuming and delicate task that tests the dexterity and perseverance of the general public, and even the most experienced repair personnel and professionals in the operating room. In addition, the placement of minuscule screws can also be a challenge in the manufacturing process of the screw systems previously described.

Therefore, a need exists for an efficient and effective fastener organization and retrieval tool.

SUMMARY

In one implementation, a screw containment system is disclosed, the system including a caddy, a first screw, an adhesive substance, and a cover. The caddy includes a first surface defining a plurality of openings including a first opening, a second surface opposite and spaced apart from the first surface, a plurality of recesses including a first recess extending from the first opening towards the second surface of the caddy, the first recess being sized to accept a screw therein, and a counterbore disposed at a distal end of the first recess. The first screw is removably disposed in the first recess. The first screw includes a head disposed on a first end and having a drive, a shank coupled to the head to define a screw head shoulder, the screw head shoulder sitting on an upper surface of the counterbore with the shank disposed in an inner recess of the counterbore, threads disposed on a portion of the shank, and a tip on a second end. The adhesive substance is disposed within the drive of the first screw, the adhesive substance being configured to temporarily couple two objects together. The cover is removably coupled to the first surface of the caddy such that, while the cover is coupled to the first surface, the first screw held within the first recess.

In some implementations, the system further includes a screwdriver having a shaft sized to fit within the first recess of the caddy and a tip sized to fit within the drive of the screw. In some implementations, a diameter of the first recess is between 0 mm and 1 mm greater than a diameter of the shaft of the screwdriver.

In some implementations, the first opening is a circle, and the first recess is a cylindrical hole. In some implementations, the first recess at least partially includes a frustoconical shape.

In some implementations, the cover is hingably or slidably coupled to the caddy. In some implementations, the cover is a removably plastic film. In some implementations, the adhesive substance is a bone wax or a putty.

In some implementations, the plurality of openings further includes a second opening and the plurality of recesses includes a second recess extending from the second opening towards the second surface of the caddy, wherein the second recess is sized to accept a second screw therein, the second screw being a same or a different size than the first screw.

In some implementations, the first screw is an eyeglass frame screw, a watch screw, a jewelry screw, an orthopedic screw or spinal screw, a screw for cranial plating, or a screw for oral and maxillofacial surgery.

In another implementation, a caddy is disclosed, the caddy including: a first surface defining a plurality of openings including a first opening and a second opening; a second surface opposite and spaced apart from the first surface; a first recess extending from the first opening towards the second surface of the caddy, the first recess being sized to fit a screw therein, the first recess having a counterbore at a distal end thereof; a screw disposed within the first recess, a shank of the screw being disposed within an inner recess of the counterbore, and a screw head shoulder of the screw sitting on an upper surface of the counterbore; a second recess extending from the second opening towards the second surface of the caddy, the second recess being sized to fit a shaft of a screwdriver therein; and an adhesive substance disposed within the second recess.

In some implementations, the caddy further includes a screwdriver having a shaft sized to fit within each of the first recess and the second recess of the caddy and a tip sized to fit within a drive of the screw. In some implementations, a diameter of the first recess is between 0 mm and 1 mm greater than a diameter of the shaft of the screwdriver. In some implementations, a diameter of the second recess is greater than a diameter of the shaft of the screwdriver.

In another implementation, a method of picking up a screw is disclosed, the method including: providing a caddy having a first surface defining a plurality of openings from which a plurality of recesses, including a first recess, extend towards a second surface, the first recess having a first screw disposed therein, the first screw having an adhesive substance disposed within a drive of a head of the screw, wherein the caddy further includes a cover removably coupled to the first surface and configured to cover the plurality of recesses; providing a screwdriver having a shank and a tip configured to engage with the drive of the screw; removing the cover from the caddy to expose the plurality of recesses; inserting the tip of the screwdriver into the first recess until the tip of the screwdriver abuts and deforms the adhesive substance such that the screw and the screwdriver are temporarily coupled together via the adhesive substance; and removing the tip of the screwdriver and the screw from the first recess.

In some implementations, the screw is an eyeglass frame screw, the method further including: inserting the screw into a screw hole of a pair of eyeglasses; and decoupling the adhesive substance and the screwdriver from the screw.

In some implementations, the screw is a wristwatch or jewelry screw, the method further including: inserting the screw into a screw hole of a wristwatch; and decoupling the adhesive substance and the screwdriver from the screw.

In some implementations, the screw is an orthopedic, spinal, cranial fixation or an oral and maxillofacial surgical screw, the method further including: inserting the screw into a screw hole of spinal implant; and decoupling the adhesive substance and the screwdriver from the screw.

In another implementation, a method of picking up a screw is disclosed, the method including: providing a caddy having a first surface defining a plurality of openings from which a plurality of recesses, including a first recess and a second recess, extend towards a second surface, the first recess having a first screw disposed therein, the second recess having an adhesive substance disposed therein, wherein the caddy further includes a cover removably coupled to the first surface and configured to cover the plurality of recesses; providing a screwdriver having a shank and a tip configured to engage with a drive of the screw; removing the cover from the caddy to expose the plurality of recesses; inserting the tip of the screwdriver into the second recess to abut and deform a portion of the adhesive substance; removing the tip of the screwdriver from the second recess along with the portion of the adhesive substance; inserting the tip of the screwdriver with the adhesive substance into the first recess until the tip of the screwdriver abuts the drive of the screw with the portion of the adhesive substance therebetween such that the screw and the screwdriver are temporarily coupled together via the adhesive substance; and removing the tip of the screwdriver and the screw from the first recess.

In some implementations, the method further includes inserting the screw into a screw hole of a pair of eyeglasses; and decoupling the adhesive substance and the screwdriver from the screw.

Additional advantages will be set forth in part in the description that follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

Figure 1A:
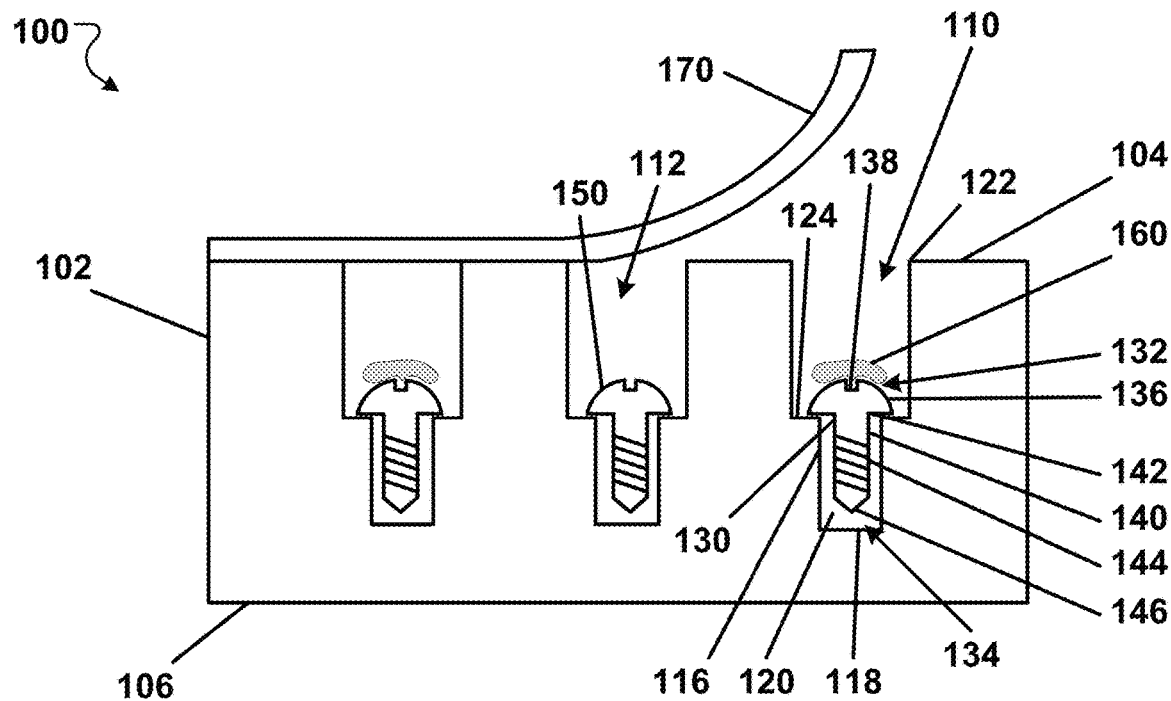
FIGS. 1A-1C show a screw containment system, according to one implementation.

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Referring generally to the figures, a screw catchment and caddy system is shown, according to various implementations.

In one aspect, the assembly and repair of small devices (e.g., wristwatches and eyeglass frames) is made difficult by the inclusion of small screws and screw holes. These screws are often on a scale of less than 1 mm, and they are difficult for a human to manipulate and align. Existing tools fail to provide a robust and firm connection between a tool and the screw. For example, magnetic-tipped screwdrivers may retain the screw close to the magnetic tip, but they often fall off to the side of the tip rather than remaining centrally aligned with the drive of the screw. Thus, the systems, methods, and devices disclosed herein provide for an improvement upon this technical problem. The systems, methods, and devices disclosed herein provide for firm, consistent, repeatable, and intuitive screw catchment. The systems, methods, and devices disclosed herein further provide for a more efficient manner of assembling and repairing small devices using these small fasteners.

In another aspect, the retrieval and placement of fasteners (e.g., small screws) in a surgical setting are made difficult by (i) the small size of the fasteners and their respective holes, and (ii) the sterile setting and the particular arrangement of components therein. While existing tools may provide an array of fasteners from which a surgeon may select, they do not address issues of alignment and firm contact between the fastener and the tool. The systems, methods, and devices disclosed herein provide for firm, consistent, repeatable, and intuitive catchment and use of surgical fasteners. The systems, methods, and devices disclosed herein provide for a more efficient manner of retrieving small fasteners from a caddy and placing them at a desired location.

While screws are contemplated as one example applicable to the systems, methods, and devices disclosed herein, this disclosure is not limited only to screws. In some implementations, the systems, methods, and devices of this disclosure apply to a variety of fasteners (e.g., nuts, bolts, nails, staples, buttons, etc.). In some implementations, the systems, methods, and devices of this disclosure apply to a variety of items considered small on the scale of human handling (e.g., building materials, craft materials, pharmaceutical materials, cooking materials, etc.).

Example Device #1

Figure 1B:
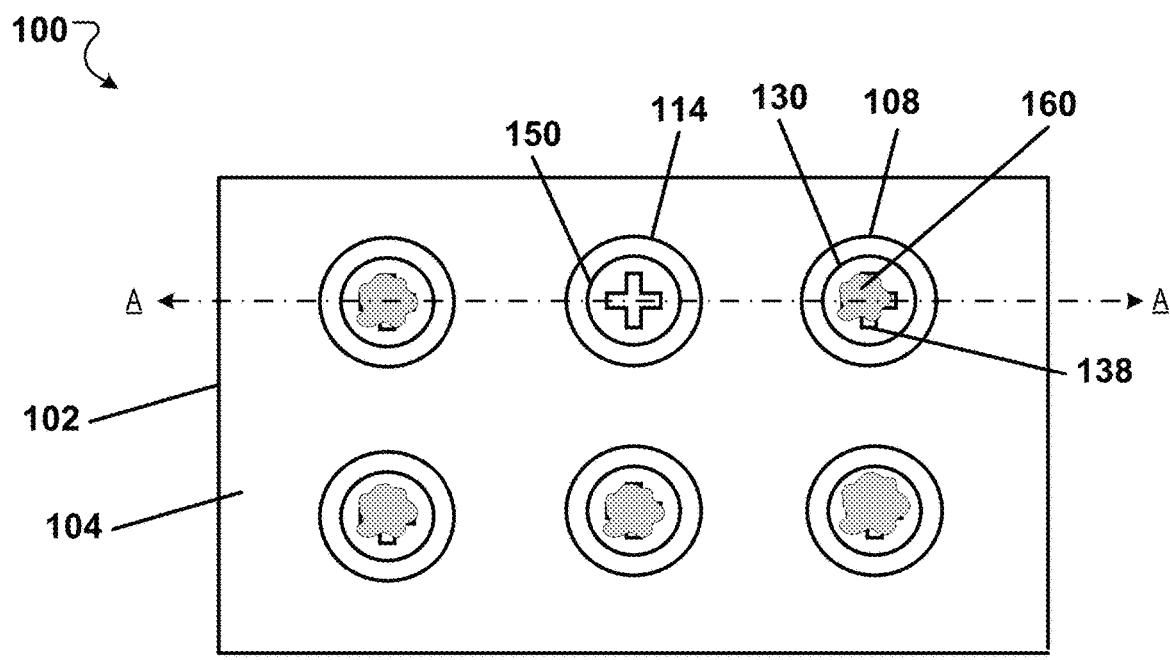
Figure 1C:
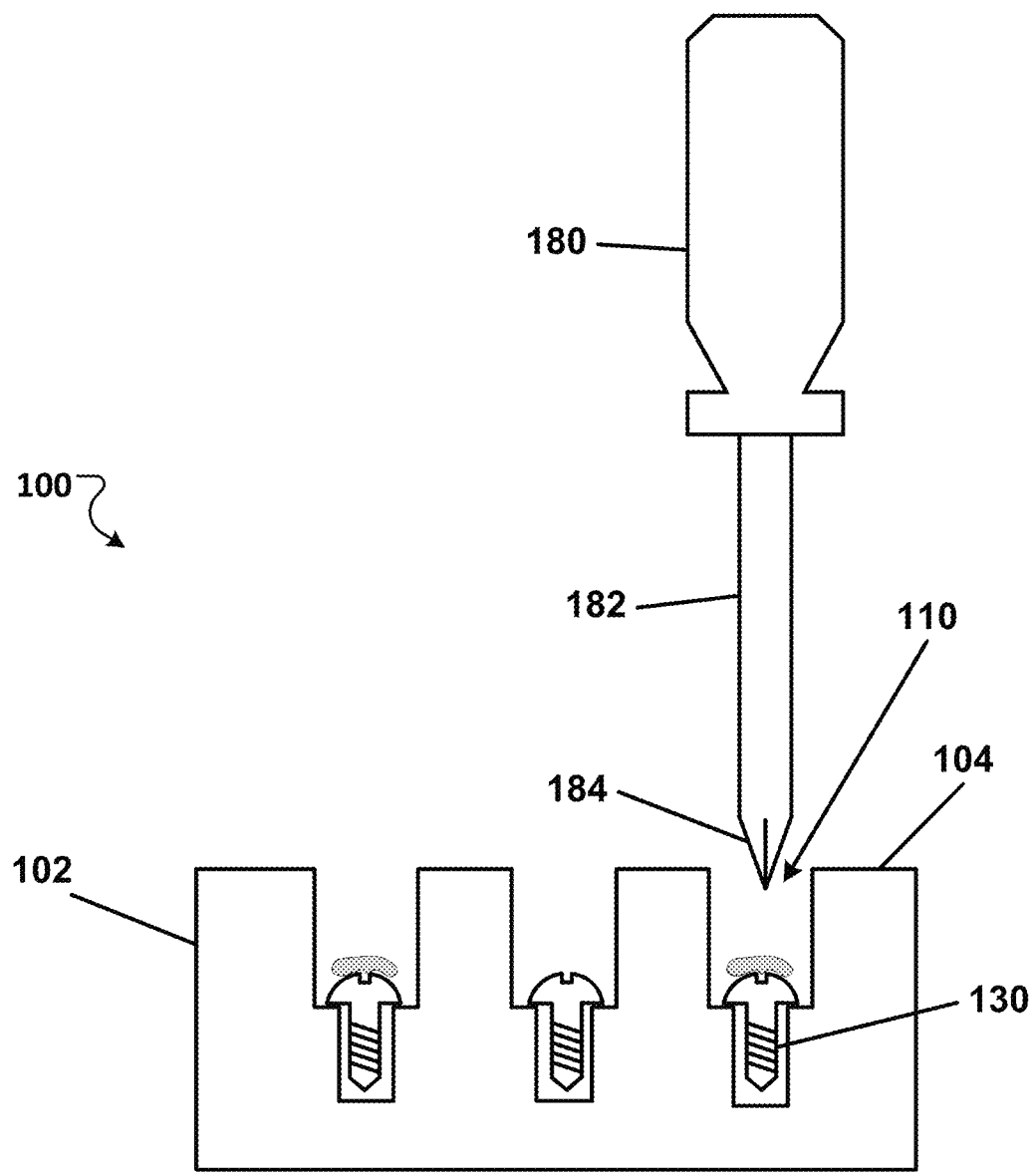

FIGS. 1A-1C show a screw containment system 100, according to one implementation. Specifically, FIG. 1A shows a cross-sectional view along line A-A in FIG. 1B, and FIG. 1B shows a top view without a cover. FIG. 1C shows the cross-sectional view of FIG. 1A along with a screwdriver 180. The screw containment system 100 of FIGS. 1A-1C includes a caddy 102, a first screw 130, a second screw 150, an adhesive substance 160, and a cover 170.

The caddy 102 includes a first surface 104 and a second surface 106 opposite and spaced apart from the first surface 104. The first surface 104 defines a plurality of openings, including a first opening 108 and a second opening 112. The caddy 102 further includes a plurality of recesses extending from the respective openings in the first surface 104 towards the second surface 106. Each recess is sized to accept a screw and/or a screwdriver therein (e.g., the screwdriver 180 of FIG. 1C). For example, a diameter of the first opening may be larger than a diameter of a screwdriver shaft. In other implementations, the diameter of the first opening is between 0 mm and 1 mm greater than the diameter of the screwdriver shaft (e.g., to prevent misalignment of the screwdriver tip with the screw drive). Each recess includes a counterbore disposed at a distal end of the recess.

The plurality of recesses includes a first recess 110 extending from the first opening 108 and a second recess 114 extending from a second opening 112. The first recess 110 includes a first counterbore 116 disposed at the distal end 118 of the first recess 110. The first counterbore 116 includes an inner recess 120 defined by the first counterbore 116 which is smaller in diameter than the portion at the proximal end 122 of the first recess 110. Thus, the first counterbore 116 defines an upper surface 124.

As shown, the caddy 102 includes six openings in the first surface 104 with six corresponding recesses. Each of the openings and corresponding recesses of the caddy 102 of system 100 is identical in size and structure. However, in other implementations, a variety of sizes, structures, numbers, and arrangements of openings and corresponding recesses are contemplated. For example, in some implementations, the caddy may define 1, 2, 3, 4, 5, 7, 8, 10, 15, 20, 30, 40, 50, or more openings and corresponding recesses. In other implementations, one opening and corresponding recess may have a larger or smaller size (e.g., diameter, depth, etc.) than an adjacent opening and corresponding recess. In other implementations, the size and dimensions of the counterbores of adjacent recesses may be different. In other implementations, some of the recesses do not include counterbores and instead include only a cylindrical or partially cylindrical recess. In other implementations, at least a portion of the recess includes a frustoconical shape (e.g., a countersink or chamfered edge on the proximal end of the recess).

The caddy 102 may comprise a transparent material (e.g., polycarbonate, acrylic, polyvinyl chloride, cyclic olefin copolymers, polypropylene, or any other substantially transparent and moldable material). Such a transparent material allows a user to see the screws in the caddy and determine which recesses are empty or filled. In other implementations, the caddy comprises a non-transparent material.

The caddy 102 includes a first screw 130 removably disposed in the first recess 110. The first screw 130 includes a head 136 disposed on a first end 132 of the screw. The head 136 defines a drive 138. A shank 140 is coupled to the head 136 to define a screw head shoulder 142. The shank 140 extends from the screw head shoulder 142 towards a second end 134 having a tip 146. The shank 140 includes threads 144 on a portion of the shank 140. As shown, the screw head shoulder 142 sits on the upper surface 124 of the first counterbore 116 while the shank 140 is disposed within the inner recess 120 of the first counterbore 116.

FIGS. 1A and 1B further include a second screw 150 that is substantially similar to the first screw 130. The second screw 150 is disposed in the second recess 114 in a similar manner as the first screw 130 in the first recess 110. The second screw 150 is shown without adhesive substance 160 on top—for clarity. However, in contemplated configurations, all of the screws of the system include an adhesive substance on top. In other configurations, some of the screws include an adhesive substance on top while others do not.

The first screw 130 and the second screw 150 of FIGS. 1A and 1B are identical in size. However, in other implementations, one screw may have a different size, shape, function, or other dimension than another screw. For example, in some implementations, one screw may have a first shaft length and another screw may have a second shaft length being longer or shorter than the first shaft length. In other implementations, a first screw may have a first drive shape (e.g., crosshead) while a second screw may have a second drive shape (e.g., hexagonal or flathead).

The first screw 130 and the second screw 150 may have a size and composition fit for a particular device or purpose. For example, in some implementations, the first and second screws are couplable and insertable into an eyeglass frame such that the system forms an eyeglass repair kit. In some implementations, the first and second screws are couplable and insertable into a piece of jewelry (e.g., a wristwatch) such that the system forms a jewelry or wristwatch repair kit. In some implementations, the first and second screws are couplable to a spinal surgery clamp and insertable into a spine or a spinal implant of a patient such that the system forms a spinal screw caddy system.

The system 100 includes the adhesive substance 160 disposed on the drive 138 of the first screw 130. For example, the adhesive substance 160 is disposed on the first end 132 of the first screw 130 with some of the adhesive substance 160 extending over a surface of the head 136 and some adhesive substance 160 extending into the drive 138. The adhesive substance 160 is configured to temporarily couple two objects together such that one object may be removed from (i) the adhesive substance and/or (ii) the second object upon an application of force or torsion. The adhesive substance 160 is not meant to permanently couple two objects together; however, in other implementations, such a configuration is contemplated by this disclosure. In some implementations, the adhesive substance is a bone wax or comprises at least one of beeswax, isopropyl palmitate, and a wax-softening agent. In some implementations, the adhesive substance is a putty (e.g., sticky, tacky, or adhesive putty). In some implementations, the adhesive substance comprises at least one of glue, water, polymer (e.g., polyvinyl acetate), and borax. In some implementations, the adhesive substance is a thermosetting plastic or elastomer.

The cover 170 is removably coupled to the first surface 104 of the caddy 102. The cover 170 is a peelable plastic cover movable from a closed configuration to an open configuration. In practice, the cover 170 prevents the screws from falling out of the caddy 102 or rearranging themselves within the recess (e.g., dislodging the shank 140 from the inner recess 120 of the counterbore 116). For example, the cover 170 keeps the inner components of the system 200 in place during transport and/or handling prior to the system 100 being used. The cover 170 comprises a transparent material (e.g., transparent plastic); however, in other implementations, the cover may not be transparent.

While the cover 170 is coupled to the first surface 104 (i.e., in the closed configuration), each of the screws of the system 100 (e.g., the first screw 130 and the second screw 150) are held within their respective recess. When the cover 170 is pulled back (i.e., moved from the closed configuration to the open configuration), each of the screws is exposed within their respective recess. In other implementations, the cover is a hingable or slidable cover configured to move back and forth between the open and closed configurations (e.g., via a latch or clip).

A screwdriver 180 is shown in FIG. 1C has a shaft 182 and a tip 184. The shaft 182 has a diameter sized to fit within each of the plurality of recesses of the caddy 102. The tip 184 is shaped to engage with the drive of the screws (e.g., the drive 138 of the first screw 130).

In use, a method of picking up a screw is disclosed using the system 100. The caddy 102 is provided with screws pre-loaded into the plurality of recesses, each screw having the adhesive substance 160 disposed on top adjacent to the drive. The screwdriver 180 is also provided having a shaft 182 and a tip 184 configured to engage with the drive of the screw (e.g., drive 138 of the first screw 130).

The cover 170 is removed from the caddy 102 to expose the plurality of recesses (including the first recess 110 and the second recess 114). The tip 184 of the screwdriver 180 is inserted into the first recess 110 until the tip 184 of the screwdriver 180 abuts and deforms the adhesive substance 160 such that the first screw 130 and the screwdriver 180 are temporarily coupled together via the adhesive substance 160. Then, the screwdriver 180 is removed from the first recess 110 along with the first screw 130 stuck to the tip 184.

Once the first screw 130 is coupled to the screwdriver 180, the first screw 130 may be easily and efficiently placed in a desired location. For example, the first screw 130 may be inserted into a screw hole of a pair of eyeglasses, a screw hole of a wristwatch, or any other jewelry piece. In other implementations, the first screw 130 may be an orthopedic screw, or a spinal screw, or a screw for cranial plating and may be inserted into a screw hole of a spinal implant or anatomical feature for oral, maxillofacial, or another type of surgery. After insertion, the first screw 130 is decoupled from the adhesive substance 160 and the screwdriver 180. For example, the decoupling step may be accomplished by pulling the screwdriver 180 out from the drive 138 of the first screw 130 along a longitudinal axis or at an angle with respect to the longitudinal axis of the first screw 130. In some implementations, the decoupling step may be accomplished by twisting the screwdriver 180 such that torsional force removes the adhesive substance 160 without moving the first screw 130 (e.g., by pulling the screwdriver 180 up out of the drive 138 without fully decoupling from the adhesive substance 160). In some implementations, the decoupling step is accomplished by a combination of the above operations (e.g., pulling and twisting at an angle).

Example Device #2

Figure 2A:
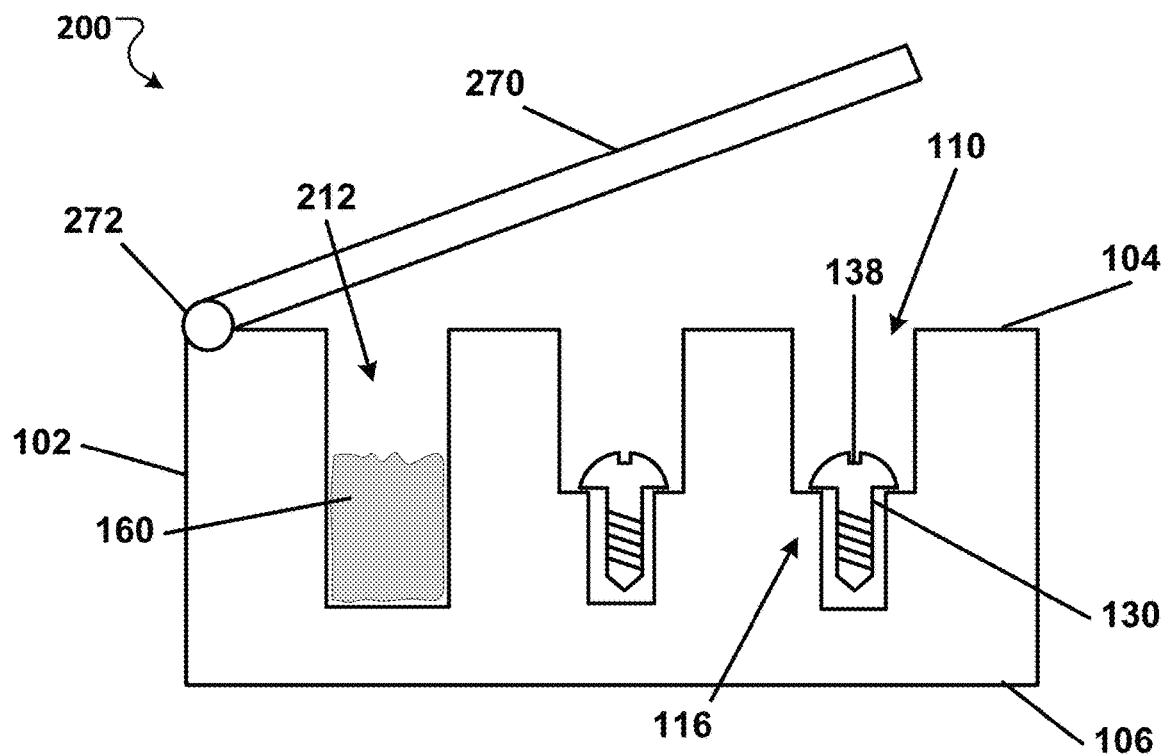
FIGS. 2A and 2B show a screw containment system, according to one implementation.
Figure 2B:
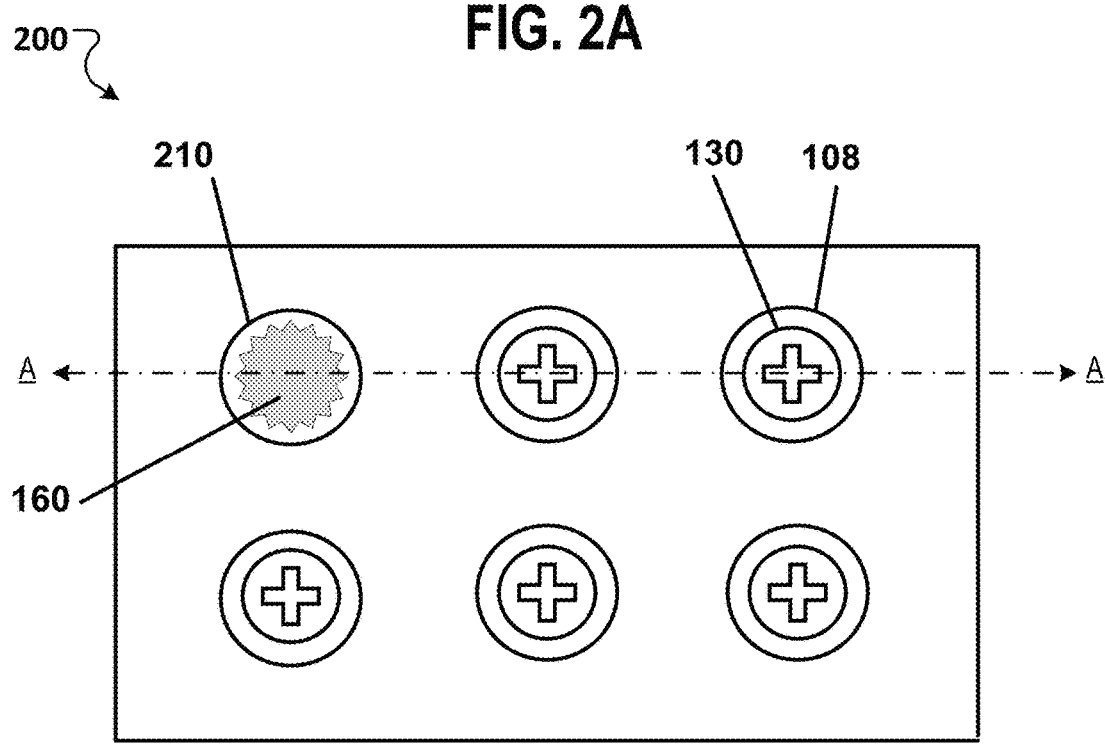

FIGS. 2A and 2B show a system 200 that is substantially similar to the system 100 of FIGS. 1A-1C except as described below. Like reference numerals between the two systems denote like elements. Specifically, FIG. 2A shows a cross-sectional view along line A-A in FIG. 2B, and FIG. 2B shows a top view without a cover. The system 200 includes a caddy 102 defining a plurality of openings that extend from a first surface 104 towards a second surface 106 to define a plurality of recesses. The plurality of recesses includes a first recess 110 extending from a first opening 108. The first recess 110 includes a first counterbore 116. A first screw 130 is disposed within the first recess 110, resting on the first counterbore 116.

The plurality of recesses further includes a second recess 212 extending from a second opening 210. The second recess 212 is sized to accept the shaft and tip of a screwdriver (e.g., the screwdriver 180 of FIG. 1C). While the second opening 210 may have a diameter matching that of the first opening 108, the second recess 212 of FIGS. 2A-2B does not match the shape and dimensions of the first recess 110. Rather, the second recess 212 is a cylindrical hole without a counterbore. In other implementations, the second recess may have a different shape (e.g., conical, frustoconical, or including a counterbore to match the first recess). In other implementations, the shape of the second opening may include a different shape (e.g., triangle, hexagon, octagon, etc.).

Rather than include the adhesive substance 160 on top of the screw heads, the system 200 includes a bulk deposit of adhesive substance 160. The second recess 212 includes the adhesive substance 160 at a greater volume than the individual deposits on the screws in system 100. Thus, the adhesive substance 160 of system 200 can be used repeatedly in small portions. In some implementations, a second, separate repository of adhesive substance (e.g., a replacement canister) is provided with the system 200 to either refill the second recess 212 or to use separately from the second recess 212.

The cover 270 in system 200 is a hinged cover 270 coupled to the caddy 102 via a hinge 272. The cover 270 is movable between an open and closed configuration. The system 200 may be closed and sealed, opened for use, and then re-closed and sealed repeatedly. Similar to the cover 170 of system 100, the cover 270 may comprise a transparent material.

In use, a method of picking up a screw is disclosed using the system 200. The caddy 102 of system 200 is provided with screws pre-loaded into the plurality of recesses (e.g., all but one of the recesses may have a screw disposed therein). A screwdriver (e.g., the screwdriver 180 shown in FIG. 1C) is also provided having a shaft 182 and a tip 184 configured to engage with the drive of the screw (e.g., drive 138 of the first screw 130).

The cover 270 is hinged or rotated away from the caddy 102 to expose the plurality of recesses. Then, the tip 184 of the screwdriver 180 is inserted into the second recess 212 to abut and deform a portion of the adhesive substance 160 therein. The tip 184 of the screwdriver 180 is removed from the second recess 212 along with a portion of the adhesive substance 160 stuck thereon.

The tip 184 of the screwdriver 180 having the adhesive substance 160 is inserted into the first recess 110 until the tip 184 abuts the drive 138 of the first screw 130. With the portion of the adhesive substance 160 therebetween, the first screw 130 and the screwdriver 180 are temporarily coupled together. The tip 184 of the screwdriver 180 is then removed from the first recess 110 with the portion of the adhesive substance 160 and the first screw 130 stuck thereon.

Once removed, the first screw 130 may be inserted into a desired location, similar to the system 100. In contrast to system 100, system 200 having the bulk deposit of adhesive substance 160 allows for a user to control the amount of adhesive substance 160 used. For example, a larger mass of adhesive substance 160 may be used on a larger screw while a smaller mass may be used for a smaller screw. Furthermore, manufacturing lines may be streamlined for one system or the other (i.e., there are some advantages to placing adhesive substance directly on the screws, and there are some advantages to providing only one recess full of adhesive substance).

Example System #3

Figure 3A:
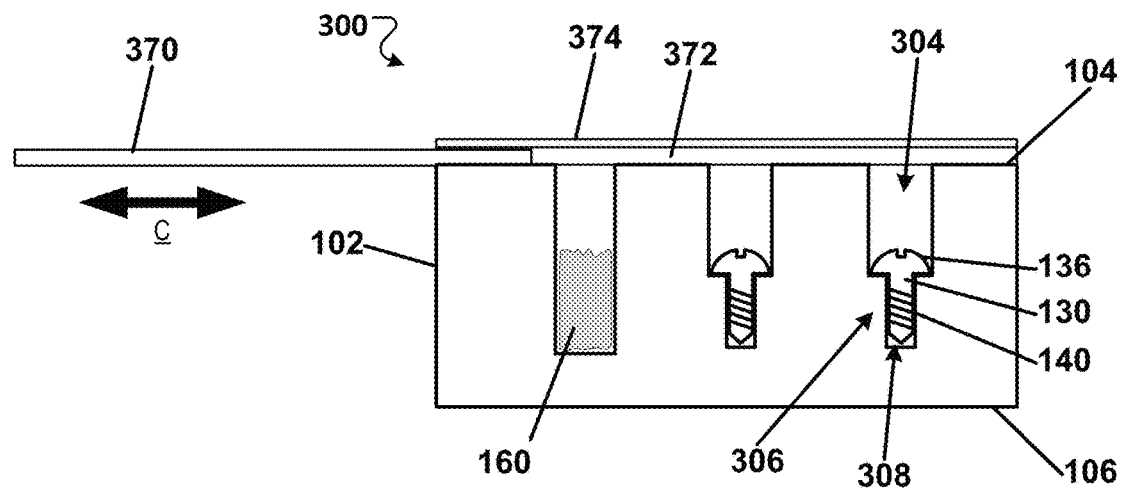
FIGS. 3A-3C show a screw containment system, according to one implementation.
Figure 3B:
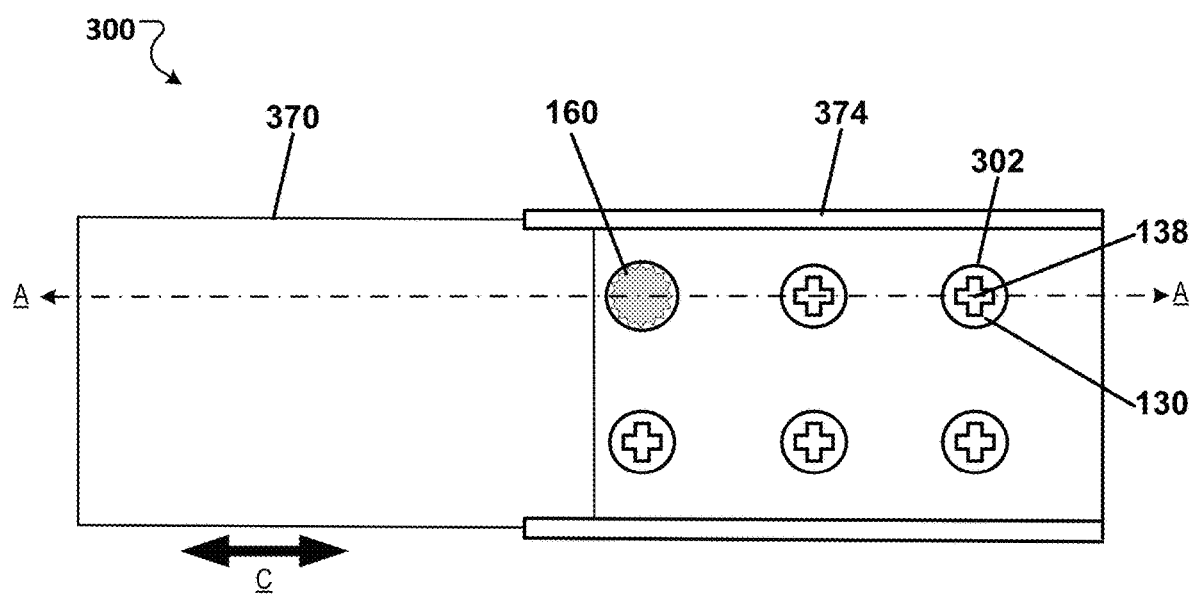
Figure 3C:
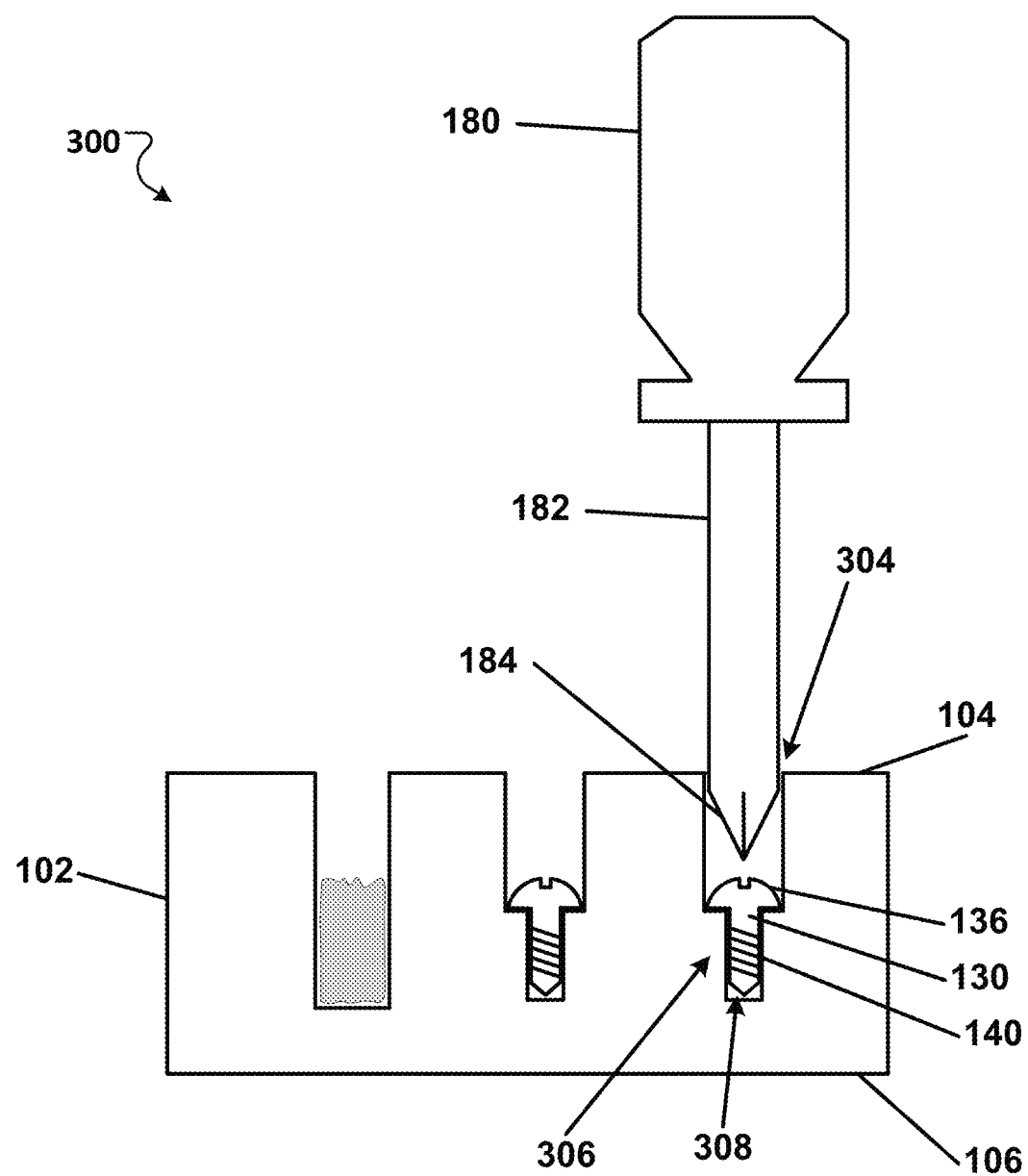

FIGS. 3A, 3B, and 3C show a system 300 substantially similar to system 200 of FIGS. 2A and 2B, except as described below. Each of the plurality of openings defined by the caddy 102 in system 300 are smaller in diameter than the plurality of openings defined by the caddy 102 in system 200. As shown, the first opening 302 and the first recess 304 extending therefrom includes the first screw 130. However, the diameter of the first opening 302 and the first recess 304 are close to or equal to the diameter of the head 136 of the first screw 130. In some implementations, the diameter of the first opening 302 and the first recess 304 are between 0 mm and 1 mm greater than the diameter of the head 136 of the first screw 130.

Furthermore, the diameter of the first opening 302 and the first recess 304 are also close to or equal to the diameter of the shaft 182 of the screwdriver 180, as shown in FIG. 3C. Similarly, the first counterbore 306 of the first recess 304 is similar to the first counterbore 116 of system 200, except that the inner recess 308 of the first counterbore 306 has a smaller diameter. As shown, the inner recess 308 of the first counterbore 306 has a diameter close to or equal to the diameter of the shank 140 of the first screw 130.

The system 300, having the closely matched dimensions described herein, allows for minimal displacement, toggle, and/or lateral movement of the various elements during the engagement process. For example, as the screwdriver 180 engages with the first screw 130, lateral misalignment is minimized or eliminated. The longitudinal axes of the screwdriver 180 and the first screw 130 are configured to be in perfect or near-perfect alignment each time. Additionally, the first screw 130 is unlikely to drift from the longitudinal alignment with the first recess 304 and the first counterbore 306 due to the tight dimensions. Therefore, the system 300 provides a user-friendly experience with minimal errors in operation.

The system 300 further includes an alternative embodiment of a cover 370 (not shown in FIG. 3C). The cover 370 slides in a groove 372 fixated to the first surface 104 via a side wall 374. The cover 370 is configured to slide back and forth in the directions marked by arrows "C" in FIGS. 3A and 3B. The cover 370 may slide along the groove 372 to completely expose the recessed screws while the cover stays parallel to surface 104. Similarly, the cover 370 may slide along the groove 372 to retain the recessed screws (e.g., for storage). Similar to the caddy 102, the cover 370 may comprise a transparent material such the number of screws remaining in the plurality of recessed may be easily determined by a user.

Configuration of Certain Implementations

The construction and arrangement of the systems and methods as shown in the various implementations are illustrative only. Although only a few implementations have been described in detail in this disclosure, many modifications are possible (e.g., variations in sizes, dimensions, structures, shapes, and proportions of the various elements, values of parameters, mounting arrangements, use of materials, colors, orientations, etc.). For example, the position of elements may be reversed or otherwise varied, and the nature or number of discrete elements or positions may be altered or varied. Accordingly, all such modifications are intended to be included within the scope of the present disclosure. The order or sequence of any process or method steps may be varied or re-sequenced according to alternative implementations. Other substitutions, modifications, changes, and omissions may be made in the design, operating conditions, and arrangement of the implementations without departing from the scope of the present disclosure.

It is to be understood that the methods and systems are not limited to specific synthetic methods, specific components, or to particular compositions. It is also to be understood that the terminology used herein is for the purpose of describing particular implementations only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another implementation includes from the one particular value and/or to the other particular value. Similarly, when values are expressed as approximations, by use of the antecedent "about," it will be understood that the particular value forms another implementation. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal implementation. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that, while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific implementation or combination of implementations of the disclosed methods.

What is claimed is:

1. A screw containment system comprising:
   a caddy comprising:
      a first surface defining a plurality of openings including a first opening;
      a second surface opposite and spaced apart from the first surf ace;
      a plurality of recesses including a first recess extending from the first opening towards the second surface of the caddy, the first recess being sized to accept a screw therein; and
      a counterbore disposed at a distal end of the first recess;
   a first screw removably disposed in the first recess, the first screw comprising:
      a head disposed on a first end and having a drive;
      a shank coupled to the head to define a screw head shoulder, the screw head shoulder sitting on an upper surf ace of the counterbore with the shank disposed in an inner recess of the counterbore;
      threads disposed on a portion of the shank; and
      a tip on a second end;
   an adhesive substance disposed within the drive of the first screw, the adhesive substance being configured to temporarily couple two objects together; and
   a cover removably coupled to the first surface of the caddy such that, while the cover is coupled to the first surface, the first screw held within the first recess.

2. The system of claim 1, further comprising a screwdriver having a shaft sized to fit within the first recess of the caddy and a tip sized to fit within the drive of the screw.

3. The system of claim 2, wherein a diameter of the first recess is between 0 mm and 1 mm greater than a diameter of the shaft of the screwdriver.

4. The system of claim 1, wherein the first opening is a circle and the first recess is a cylindrical hole.

5. The system of claim 1, wherein the first recess at least partially comprises a frustoconical shape.

6. The system of claim 1, wherein the cover is a removable plastic film.

7. The system of claim 1, wherein the adhesive substance is a bone wax or a putty.

8. The system of claim 1, wherein the plurality of openings further comprises a second opening and the plurality of recesses includes a second recess extending from the second opening towards the second surface of the caddy, wherein the second recess is sized to accept a second screw therein, the second screw being a same or a different size than the first screw.

9. The system of claim 1, wherein the first screw is an eyeglass frame screw, a watch screw, a jewelry screw, an orthopedic screw, a spinal screw, or a screw for cranial plating, oral surgery, or maxillofacial surgery.

* * * * *